United States Patent [19]
Dell et al.

[11] Patent Number: 4,994,541
[45] Date of Patent: Feb. 19, 1991

[54] PROCESS FOR THE PREPARATION OF POLYISOCYANATES CONTAINING URETDIONE AND ISOCYANURATE GROUPS, THE POLYISOCYANATES OBTAINED BY THIS PROCESS AND THEIR USE IN TWO-COMPONENT POLYURETHANE COATINGS

[75] Inventors: Winfried Dell; Werner Kubitza; Dietrich Liebsch, all of Leverkusen, Fed. Rep. of Germany

[73] Assignee: Bayer Aktiengesellschaft, Leverkusen, Fed. Rep. of Germany

[21] Appl. No.: 455,693

[22] Filed: Dec. 22, 1989

[30] Foreign Application Priority Data

Jan. 3, 1989 [DE] Fed. Rep. of Germany ....... 3900053

[51] Int. Cl.$^5$ ............................................. C08G 18/38
[52] U.S. Cl. ........................................ 528/51; 528/67; 528/38; 521/108
[58] Field of Search ............................ 528/51, 67, 38; 521/108, 168, 906

[56] References Cited

U.S. PATENT DOCUMENTS

| | | | |
|---|---|---|---|
| 3,489,744 | 1/1970 | Schwarcz et al. | 260/239 |
| 3,645,979 | 2/1972 | Liebsch et al. | 260/77.5 |
| 3,919,195 | 11/1975 | Bakhitov et al. | 260/239 |
| 4,294,719 | 10/1981 | Wagner et al. | 528/67 |
| 4,344,855 | 8/1982 | Schäfer et al. | 528/51 |
| 4,521,338 | 6/1985 | Grögler et al. | 260/239 |
| 4,614,785 | 9/1986 | Richter et al. | 528/45 |
| 4,623,672 | 11/1986 | Kleinstück et al. | 528/51 |
| 4,668,780 | 5/1987 | Disteldorf et al. | 540/202 |

FOREIGN PATENT DOCUMENTS 1934763 1/1971 Fed. Rep. of Germany .
1153815 5/1969 United Kingdom .
1244416 9/1971 United Kingdom .

Primary Examiner—John Kight, III
Assistant Examiner—Duc Truong
Attorney, Agent, or Firm—Joseph C. Gil; Thomas W. Roy

[57] ABSTRACT

The present invention is directed to a process for the preparation of modified polyisocyanates containing uretdione and isocyanurate groups by the oligomerization of a portion of the isocyanate groups of organic diisocyanates containing (cyclo)aliphatically-bound isocyanate groups in the presence of organic phosphines of catalysts followed by termination of the oligomerization reaction at the desired degree of oligomerization by the addition of a catalyst poison and removal, by distillation, of at least a portion of the excess, unreacted starting diisocyanate, characterized in that (a) about 0.1 to 10% of the isocyanate groups present in the starting diisocyanate are converted into urethane groups by the addition of at least one alcohol before and/or during the oligomerization reaction, and
(b) the distillation residue obtained after removal of the excess starting diisocyanate is heated to temperatures of at least 50° C. in the presence of 100 to 10,000 ppm, based on the weight of the distillation residue, of a peroxide.

The present invention is also directed to the polyisocyanates containing uretdione and isocyanurate groups obtained by this process and their use, optionally in blocked form, as the isocyanate component in two-component polyurethane coatings.

18 Claims, No Drawings

PROCESS FOR THE PREPARATION OF POLYISOCYANATES CONTAINING URETDIONE AND ISOCYANURATE GROUPS, THE POLYISOCYANATES OBTAINED BY THIS PROCESS AND THEIR USE IN TWO-COMPONENT POLYURETHANE COATINGS

BACKGROUND OF THE INVENTION

1. Field of the Invention

The present invention is directed to an improved process for the preparation of (cyclo)aliphatic polyisocyanates containing uretdione and isocyanurate groups from (cyclo)aliphatic diisocyanates with the aid of tertiary phosphine catalysts, to the modified polyisocyanates obtained by this process and to their use as the isocyanate component in two-component polyurethane coatings.

2. Description of the Prior Art

The preparation of lacquer polyisocyanates containing uretdione and isocyanurate groups by the oligomerization of monomeric starting diisocyanates with the aid of organic phosphines as catalysts followed by termination of the modifying reaction at the desired degree of oligomerization is known (see e.g. DE-OS 1,670,667, DE-OS 1,670,720, DE-OS 1,954,093 or US-PS 4,614,785). The polyisocyanates containing uretdione and isocyanurate groups obtained by the processes described in these prior publications generally have an iodine color number of at least 5, which limits their usefulness for light colored polyurethane lacquers.

Therefore, it is an object of the present invention to improve the processes disclosed in these prior publications for the preparation of polyisocyanates containing uretdione and isocyanurate groups from (cyclo)aliphatic starting diisocyanates so that the products obtained have iodine color numbers of at most 3, preferably 0 to 1, or Hazen color numbers according to DIN 53 409 of not more than 250, preferably below 100.

This object may be achieved by the process according to the invention described below.

SUMMARY OF THE INVENTION

The present invention is directed to a process for the preparation of modified polyisocyanates containing uretdione and isocyanurate groups by the oligomerization of a portion of the isocyanate groups of organic diisocyanates containing (cyclo)aliphatically-bound isocyanate groups in the presence of organic phosphines of catalysts followed by termination of the oligomerization reaction at the desired degree of oligomerization by the addition of a catalyst poison and removal, by distillation, of at least a portion of the excess, unreacted starting diisocyanate, characterized in that
  (a) about 0.1 to 10% of the isocyanate groups present in the starting diisocyanate are converted into urethane groups by the addition of at least one alcohol before and/or during the oligomerization reaction, and
  (b) the distillation residue obtained after removal of the excess starting diisocyanate is heated to temperatures of at least 50° C. in the presence of 100 to 10,000 ppm, based on the weight of the distillation residue, of a peroxide.

The present invention is also directed to the polyisocyanates containing uretdione and isocyanurate groups obtained by this process and their use, optionally in blocked form, as the isocyanate component in two-component polyurethane coatings.

DETAILED DESCRIPTION OF THE INVENTION

The starting materials for the process according to the invention are monomeric (cyclo)aliphatic diisocyanates having a molecular weight below 300. In accordance with the present invention "(cyclo)aliphatic" diisocyanates are diisocyanates containing aliphatically-bound isocyanate groups, cycloaliphatically-bound isocyanate groups or both aliphatically-bound and cycloaliphatically-bound isocyanate groups. Examples of these diisocyanates include 1,4-diisocyanatobutane, 1,6-diisocyantohexane (HDI), 1,12-diisocyanatododecane, 1-isocyanato-3,3,5-trimethyl-5-isocyanatomethylcyclohexane (IPDI), 4,4'-diisocyanatodicyclohexylmethane or any mixtures of such (cyclo)aliphatic diisocyanates. HDI is particularly preferred as starting diisocyanate.

Partial urethanization of the starting diisocyanates may be carried out with any organic compounds which contain an alcoholic hydroxyl group but are otherwise inert under the conditions of the process according to the invention; however, the compounds used for this modification are preferably low molecular weight, monohydric or polyhydric alcohols, in particular those with molecular weights of 32 to 200, or any mixtures of such alcohols. Examples of suitable alcohols include methanol, ethanol, n-propanol, isopropanol, n-butanol, n-hexanol, 2-ethyl-1-hexanol, ethylene glycol, propylene glycol, the isomeric butane diols, the isomeric hexane diols, the isomeric octane diols, diethylene glycol, dipropylene glycol, glycerol, trimethylol propane and any mixtures of such alcohols.

The catalysts may be any tertiary phosphines, for example the compounds mentioned in US-PS 4,614,785, column 4, lines 11 to 47, herein incorporated by reference. Tri-n-butyl-phosphine is a particularly preferred catalyst.

Suitable catalyst poisons are those previously used for this purpose, e.g., sulphur, alkylating agents such as dimethyl sulphate, p-toluene sulphonic acid methyl ester or sulphonyl isocyanates of the type disclosed in US-PS 4,614,785, column 5, line 27 to column 6, line 35, herein incorporated by reference.

The peroxides used in the last stage of the process according to the invention may be either inorganic peroxides such as hydrogen peroxide or organic peroxides such as butanone peroxide, dicumyl peroxide, dilauryl peroxide, tert.-butyl hydroperoxide, cumene hydroperoxide or dibenzoyl peroxide. Butanone peroxide is preferred.

The process according to the present invention is preferably conducted under an inert gas atmosphere (e.g., nitrogen), at least until the oligomerization reaction has been terminated. During the process about 0.1 to 10%, preferably about 0.5 to 5% of the isocyanate groups present in the starting diisocyanate are converted into urethane groups by the addition of one or more alcohols of the type exemplified above. This may be carried out by adding the alcohol at room temperature to the diisocyanate and then optionally heating, for example, at temperatures of up to 100° C., to accelerate the urethanization reaction.

At the same time or immediately thereafter, oligomerization of the partly urethanized starting diisocyanate is carried out with the addition of catalyst. The tertiary phosphines used as catalysts are generally introduced in a quantity of about 0.1 to 5.0% by weight, preferably about 0.2 to 2.0% by weight, based on the weight of the unmodified starting diisocyanate. The modifying reaction is generally carried out at a temperature about 20° to 100° C., preferably about 50° to 80° C. It is not necessary to complete the urethanization reaction before the catalyst is added. The two reactions may at least partly take place simultaneously.

When the desired degree of oligomerization has been achieved (degree of oligomerization=percentage of isocyanate groups of the urethane-modified starting diisocyanate which react to undergo dimerization or trimerization), the reaction is terminated by the addition of a catalyst poison. This termination of the reaction is generally carried out at a degree of oligomerization of about 10 to 80%, preferably about 20 to 30%. The quantity of catalyst poison required to terminate the reaction depends upon the quantity of trimerization catalyst used. However, because of catalyst losses during the reaction, about 20 to 80 equivalents of catalyst poison, based on the quantity of catalyst introduced at the beginning of the reaction, is generally sufficient.

After termination of the reaction, the major portion of unreacted excess starting diisocyanate is removed by distillation in known manner and preferably reused for another reaction batch. Distillation may be carried out, for example, in vertical pipe evaporators or thin layer evaporators conventionally used for this purpose. The distillation residues obtained generally contain a residue of monomeric starting diisocyanates of less than 2% by weight, preferably less than 0.5% by weight.

In the last stage of the process according to the invention, the distillation residue obtained is subjected to a heat treatment in the presence of a peroxide. For this purpose, the distillation residue is mixed with at least one of the peroxides exemplified above in a total quantity of about 100 to 10,000 ppm (by weight), preferably about 500 to 2000 ppm, based on the weight of the distillation residue. The mixture of distillation residue and peroxide is subsequently heated to a temperature of at least about 50°C., preferably about 50° to 120° C., for at least 20 minutes, preferably about 30 to 90 minutes.

The modified polyisocyanates obtained in accordance with the process of the present invention, especially when 1,6-diisocyanatohexane is used as the starting diisocyanate, have an isocyanate content of about 20 to 24% by weight, a urethane group content (calculated as —NH—CO—O—) of about 1 to 5% by weight, an iodine color number according to DIN 6162 of 0 to 3 and a Hazen color number according to DIN 53 409 of less than 250. The molar ratio of uretdione groups to isocyanurate groups is generally about 1:1 to 4:1. The viscosity of these products at 23° C. is generally about 100 to 300 mPa.s.

The products of the process according to the invention, in particular the preferred products according to the invention based on 1,6-diisocyanatohexane, are particularly valuable lacquer polyisocyanates. These products, optionally in the form of products blocked with reversible, monofunctional blocking agents for isocyanate groups, may be combined in known manner with organic polyhydroxyl compounds, in particular organic polyhydroxypolyesters or polyhydroxypolyacrylates to form high quality two-component polyurethane coating compositions.

The invention is further illustrated but is not intended to be limited by the following examples in which all parts and percentages are by weight unless otherwise specified. All the percentages given in the following examples are percentages by weight.

EXAMPLES EXAMPLE 1

(a) Urethanization followed by oligomerization 1344 g (4 moles) of 1,6-diisocyanatohexane were introduced into a suitable reaction vessel under anhydrous nitrogen and stirred together with 13.4 g (0.092 moles) of 2,2,4-trimethylpentane-1,3-diol at room temperature. The mixture was then heated to 60° C. and left at this temperature until the reaction between the isocyanate groups and hydroxyl groups was complete. 4.0 g (0.02 moles) of tri-n-butylphosphine were then added. The temperature was kept at 60° C. during the exothermic reaction by external cooling. After stirring for 6 hours at 60° C., the isocyanate content had fallen to about 39%. The reaction was stopped by the addition of 2.8 g (0.015 moles) of toluene sulphonic acid methyl ester and a two hour thermal after-treatment at 80° C. Unreacted starting diisocyanate was then distilled off in a thin layer evaporator at 150° C. and a pressure of below 0.5 bar. The reaction product obtained as sump product had a residual monomer content of less than 0.5% of unreacted starting diisocyanate, an iodine color number of 1, an isocyanate content of 21.6% and a viscosity of 150 mPa.s (23° C.).

The unreacted starting diisocyanate obtained was subsequently reused with fresh 1,6-diisocyanatohexane for carrying out the described reaction. This procedure was repeated a total of 20 times (20 reaction cycles). The distillation residue obtained at the end of the 20th reaction cycle was a product with a low monomer content and an iodine color number of 3. This product was subsequently worked up in accordance with the invention. The following example shows that even with an initially high iodine color number, the products eventually obtained from the process of the present invention have an exceptionally low Hazen color number.

(b) Heat treatment in the presence of a peroxide 80 parts by weight of the distillation residue having an iodine color number of 3 and obtained in Example (1a) were mixed in four parallel experiments with 250, 500, 100 and 2,500 ppm (by weight), respectively, of butanone peroxide in a suitable reaction vessel. The butanone peroxide was used in the form of a 50% by weight solution in dimethyl phthalate; the quantities set forth are based on the amount of butanone peroxide excluding solvent. The samples thus obtained were each heated to 100° C. for 1 hour. Table 1 shows the dependence of the color numbers on the quantity of peroxide.

TABLE 1

| ppm of peroxide | iodine color number | Hazen color number |
|---|---|---|
| — | 3 | — |
| 250 | 2 | — |
| 500 | 1-2 | — |
| 1000 | 1 | 150 |
| 2500 | <1 | 125 |

An increase in the duration of the above described heat treatment to a total of 4 hours led to further lightening of the color of the product. This is shown in Table 2 below.

TABLE 2

| Time (h) | Temp (°C.) | Peroxide (ppm) | | | | | | | |
|---|---|---|---|---|---|---|---|---|---|
| | | 250 Color Number | | 500 Color Number | | 1000 Color Number | | 2500 Color Number | |
| | | Iodine | Hazen | Iodine | Hazen | Iodine | Hazen | Iodine | Hazen |
| 0 | RT | 3 | — | | | | | | |
| 1 | 100 | 2 | — | 1–2 | | 1 | 150 | <1 | 125 |
| 2 | 100 | 1 | 150 | <1 | 125 | <1 | 125 | <1 | 100 |
| 4 | 100 | <1 | 125 | <1 | 125 | <1 | 100 | <1 | 60 |

In another experimental series, the temperature and the duration of the heat treatment were varied while the quantity of peroxide (500 ppm of butanone peroxide) was kept the same. The results obtained are summarized in Table 3.

TABLE 3

| Time (h) | 50° C. Color Number | | 75° C. Color Number | | 100° C. Color Number | |
|---|---|---|---|---|---|---|
| | Iodine | Hazen | Iodine | Hazen | Iodine | Hazen |
| 1 | 2 | — | 2 | — | 1–2 | — |
| 2 | 1–2 | — | 1–2 | — | <1 | 125 |
| 4 | 1 | 150 | 1–2 | 150 | <1 | 125 |

The peroxides were varied in another experimental series. The following peroxides were used: butanone peroxide (50% solution in dimethyl phthalate), dicumyl peroxide (50% solution in ethyl acetate), dilauryl peroxide (30% solution in methylene chloride), tert.-butyl hydroperoxide (50% solution in ethyl acetate), cumene hydroperoxide (50% solution in ethyl acetate), dibenzoyl peroxide (20% solution in methylene chloride) and hydrogen peroxide (30% solution in water). The peroxides were used in quantities corresponding to a concentration of 75 ppm of active oxygen (O). Therefore, in all cases the quantity of peroxide used, based on its total weight, was within the range of 100 to 10,000 ppm. The results are summarized in the following Table 4.

TABLE 4

| Time (h) | Temp. (°C) | Peroxide | Iodine Colour Number |
|---|---|---|---|
| 0 | RT | — | 3 |
| 2 | 100 | — | 3–4 |
| 2 | 100 | butanone peroxide | 1–2 |
| 2 | 100 | dicumyl peroxide | 2 |
| 2 | 100 | dilauryl peroxide | 2 |
| 2 | 100 | tert.-butyl peroxide | 2 |
| 2 | 100 | cumene hydroperoxide | 2 |
| 2 | 100 | dibenzoyl peroxide | 2 |
| 2 | 100 | hydrogen peroxide | 2 |

When the alcohol component used was varied, i.e., when equivalent quantities of diethylene glycol, butane-1,3-diol, 2-ethylhexane-1,3-diol, 2-ethylhexanol-(1), isopropanol and methanol were used in place of 2,2,4-trimethylpentane-1,3-diol, the results obtained were substantially identical.

EXAMPLE 2

(a) Urethanization and oligomerization 2000 kg of 1,6-diisocyanatohexane were introduced into a suitable reaction vessel and heated to 50° C. 20 kg of 2,2,4-trimethylpentane-1,3-diol were then introduced with continuous stirring under a nitrogen atmosphere, followed by 30 kg of tri-n-butyl phosphine. The temperature of the exothermic reaction was maintained at 60° C. by cooling. After a reaction time of 6 hours, the reaction mixture had an isocyanate content of 42.5%. The reaction was stopped at this stage by the addition of 16.5 kg of toluene sulphonic acid methyl ester and a 2 hour thermal after-treatment at 80° C. The crude product obtained was then freed from excess starting diisocyanate by evaporation in a vertical pipe evaporator (165° C./1 mbar) and thin layer evaporator (150° C./0.30 mbar). The resulting product had the following properties:

NCO content: 21.6
viscosity (mPa.s/23° C.): <200
Hazen color number: <100
unreacted starting diisocyanate: 0.5

(b) Thermal after-treatment in the presence of a peroxide

The crude product obtained according to Example (2a) was mixed with 500 ppm (by weight) of butanone peroxide. The butanone peroxide was used in the form of a A 50% solution in dimethyl phthalate; the quantity given is based on the amount of butanone peroxide excluding solvent. The resulting mixture is heated to 80° C. for 1 hour. A Hazen color number below 40 is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a modified polyisocyanate containing uretdione and isocyanurate groups which comprises
   (a) oligomerizing a portion of the isocyanate groups of an organic diisocyanate containing (cyclo)aliphatically-bound isocyanate groups in the presence of an organic phosphine catalyst,
   (b) reacting about 0.1 to 10% of the isocyanate groups present in the starting diisocyanate with at least one alcohol to form urethane groups before and/or during the oligomerization reaction of step (a),
   (c) terminating the oligomerization reaction at the desired degree of oligomerization by the addition of a catalyst poison,
   (d) subsequently removing by distillation at least a portion of the excess, unreacted starting diisocyanate and
   (e) heating the distillation residue obtained in step (d) to a temperature of at least 50° C. in the presence of about 100 to 10,000 ppm, based on the weight of said distillation residue, of a peroxide.

2. The process of claim 1 wherein said organic diisocyanate comprises 1,6-diisocyanatohexane.

3. The process of claim 1 wherein said alcohol comprises at least one monohydric or polyhydric alcohol having a molecular weight of 32 to 200.

4. The process of claim 2 wherein said alcohol comprises at least one monohydric or polyhydric alcohol having a molecular weight of 32 to 200.

5. The process of claim 1 wherein said peroxide comprises butanone peroxide.

6. The process of claim 2 wherein said peroxide comprises butanone peroxide.

7. The process of claim 3 wherein said peroxide comprises butanone peroxide.

8. The process of claim 4 wherein said peroxide comprises butanone peroxide.

9. A modified polyisocyanate containing uretdione and isocyanurate groups which is prepared by a process which comprises
   (a) oligomerizing a portion of the isocyanate groups of an organic diisocyanate containing (cyclo)aliphatically-bound isocyanate groups in the presence of an organic phosphine catalyst,
   (b) reacting about 0.1 to 10% of the isocyanate groups alcohol to form urethane groups before and/or during the oligomerization reaction of step (a),
   (c) terminating the oligomerization reaction at the desired degree of oligomerization by the addition of a catalyst poison followed,
   (d) removing by distillation at least a portion of the excess, unreacted starting diisocyanate and
   (e) heating the distillation residue obtained in step (d) to a temperature of at least 50° C. in the presence of about 100 to 10,000 ppm, based on the weight of said distillation residue, of a peroxide.

10. The modified polyisocyanate of claim 9 wherein said organic diisocyanate comprises 1,6-diisocyanatohexane.

11. The modified polyisocyanate of claim 9 wherein said alcohol comprises at least one monohydric or polyhydric alcohol having a molecular weight of 32 to 200.

12. The modified polyisocyanate of claim 10 wherein said alcohol comprises at least one monohydric or polyhydric alcohol having a molecular weight of 32 to 200.

13. The modified polyisocyanate of claim 9 wherein said peroxide comprises butanone peroxide.

14. The modified polyisocyanate of claim 10 wherein said peroxide comprises butanone peroxide.

15. The modified polyisocyanate of claim 11 wherein said peroxide comprises butanone peroxide.

16. The modified polyisocyanate of claim 12 wherein said peroxide comprises butanone peroxide.

17. A two-component polyurethane coating composition which comprises the modified polyisocyanate of claim 9 and an organic polyhydroxyl compound.

18. The coating composition of claim 17 wherein at least a portion of the isocyanate groups of said modified polyisocyanate are blocked with a reversible, monofunctional blocking agent.

* * * * *